(12) United States Patent
Raichman

(10) Patent No.: US 11,696,598 B2
(45) Date of Patent: Jul. 11, 2023

(54) VAPORIZER FOR VAPORIZING A CONSTITUENT OF A PLANT MATERIAL

(71) Applicant: Altria Client Services LLC, Richmond, VA (US)

(72) Inventor: Yossef Raichman, Herzliya (IL)

(73) Assignee: Altria Client Services LLC, Richmond, VA (US)

( * ) Notice: Subject to any disclaimer, the term of this patent is extended or adjusted under 35 U.S.C. 154(b) by 271 days.

(21) Appl. No.: 16/796,253

(22) Filed: Feb. 20, 2020

(65) Prior Publication Data
US 2020/0179625 A1 Jun. 11, 2020

Related U.S. Application Data

(60) Continuation of application No. 16/227,026, filed on Dec. 20, 2018, now Pat. No. 11,058,834, which is a
(Continued)

(51) Int. Cl.
*A61M 15/06* (2006.01)
*A61M 11/04* (2006.01)
(Continued)

(52) U.S. Cl.
CPC .............. *A24F 40/42* (2020.01); *A24F 40/40* (2020.01); *A24F 40/46* (2020.01); *A24F 40/51* (2020.01);
(Continued)

(58) Field of Classification Search
CPC .............. A61M 11/042; A61M 11/044; A61M 15/0021; A61M 15/0028; A61M 15/06;
(Continued)

(56) References Cited

U.S. PATENT DOCUMENTS

| 855,984 | A | 6/1907 | Russell |
| 1,071,389 | A | 8/1913 | Blosser |

(Continued)

FOREIGN PATENT DOCUMENTS

| CA | 2938413 A1 | 8/2015 |
| CA | 2953069 A1 | 1/2016 |

(Continued)

OTHER PUBLICATIONS

Office Action for corresponding U.S. Appl. No. 14/662,607 dated Feb. 23, 2018.
(Continued)

*Primary Examiner* — Joseph D. Boecker
(74) *Attorney, Agent, or Firm* — Harness, Dickey & Pierce, P.L.C.

(57) ABSTRACT

Apparatus and methods are described for use with a vaporizer that vaporizes at least one active ingredient of a plant material. In response to receiving a first input to the vaporizer, the plant material is heated, in a first heating step. An indication of the temperature of the plant material is detected, and, in response to detecting an indication that the temperature of the plant material is at a first temperature, the first heating step is terminated, by withholding causing further temperature increase of the plant material. The first temperature is less than 95 percent of the vaporization temperature of the active ingredient. Subsequently, a second input is received at the vaporizer. In response thereto, the plant material is heated to the vaporization temperature, in a second heating step. Other applications are also described.

20 Claims, 9 Drawing Sheets

Related U.S. Application Data division of application No. 14/662,607, filed on Mar. 19, 2015, now Pat. No. 10,179,215.

(51) Int. Cl.

| | |
|---|---|
| *A24F 40/46* | (2020.01) |
| *A24F 40/42* | (2020.01) |
| *A24F 40/57* | (2020.01) |
| *A24F 40/20* | (2020.01) |
| *A61M 15/00* | (2006.01) |
| *G05D 23/19* | (2006.01) |
| *A24F 40/51* | (2020.01) |
| *A24F 40/40* | (2020.01) |
| *A61M 16/00* | (2006.01) |

(52) U.S. Cl.
CPC ........... *A24F 40/57* (2020.01); *A61M 11/042* (2014.02); *A61M 11/044* (2014.02); *A61M 15/003* (2014.02); *A61M 15/0063* (2014.02); *A61M 15/0085* (2013.01); *A61M 15/06* (2013.01); *G05D 23/1904* (2013.01); *A24F 40/20* (2020.01); *A61M 2016/0021* (2013.01); *A61M 2016/0039* (2013.01); *A61M 2205/3368* (2013.01); *A61M 2205/3653* (2013.01); *A61M 2205/8206* (2013.01)

(58) Field of Classification Search
CPC .......... A24F 40/10; A24F 40/20; A24F 40/40; A24F 40/42; A24F 40/46; A24F 40/57; A24F 40/65
See application file for complete search history.

(56) References Cited

U.S. PATENT DOCUMENTS

| | | | |
|---|---|---|---|
| 1,934,887 A | 11/1933 | Robinson | |
| 4,214,146 A | 7/1980 | Schimanski | |
| 4,564,748 A | 1/1986 | Gupton | |
| 4,947,874 A | 8/1990 | Brooks et al. | |
| 4,947,875 A | 8/1990 | Brooks et al. | |
| 5,372,128 A | 12/1994 | Haber et al. | |
| 5,388,572 A | 2/1995 | Mulhauser et al. | |
| 5,388,573 A | 2/1995 | Mulhauser et al. | |
| 5,441,060 A | 8/1995 | Rose et al. | |
| 5,460,173 A | 10/1995 | Mulhauser et al. | |
| 5,593,792 A | 1/1997 | Farrier et al. | |
| 5,619,984 A | 4/1997 | Hodson et al. | |
| 5,645,050 A | 7/1997 | Zierenberg et al. | |
| 5,665,262 A | 9/1997 | Hajaligol et al. | |
| 5,823,182 A | 10/1998 | Van Oort | |
| 6,006,747 A | 12/1999 | Eisele et al. | |
| 6,065,472 A | 5/2000 | Anderson et al. | |
| 6,095,153 A | 8/2000 | Kessler et al. | |
| 6,481,437 B1 | 11/2002 | Pate | |
| 7,186,958 B1 | 3/2007 | Nelson | |
| 7,997,280 B2 | 8/2011 | Rosenthal | |
| 8,488,952 B2 | 7/2013 | Landry | |
| 8,490,627 B2 | 7/2013 | Levin et al. | |
| 8,714,150 B2 | 5/2014 | Alelov | |
| 8,910,630 B2 | 12/2014 | Todd | |
| 9,380,813 B2 † | 7/2016 | McCullough | |
| 9,775,379 B2 | 10/2017 | Davidson et al. | |
| 9,943,114 B2 † | 4/2018 | Batista | |
| 10,039,321 B2 † | 8/2018 | Verleur | |
| 10,179,215 B2 | 1/2019 | Raichman | |
| 10,247,443 B2 | 4/2019 | Flick | |
| 10,602,776 B2 | 3/2020 | Batista | |
| 2001/0020472 A1 | 9/2001 | Horlin | |
| 2004/0159322 A1 | 8/2004 | Kladders et al. | |
| 2005/0063686 A1 | 3/2005 | Whittle et al. | |
| 2007/0045288 A1 | 3/2007 | Nelson | |
| 2007/0102013 A1 | 5/2007 | Adams et al. | |
| 2008/0073558 A1 | 3/2008 | Howell et al. | |
| 2008/0149118 A1 † | 6/2008 | Oglesby | |
| 2009/0293888 A1 | 12/2009 | Williams et al. | |
| 2009/0293892 A1 | 12/2009 | Williams et al. | |
| 2010/0012118 A1 | 1/2010 | Storz | |
| 2010/0024834 A1 | 2/2010 | Oglesby et al. | |
| 2010/0059070 A1 | 3/2010 | Potter et al. | |
| 2010/0078022 A1 | 4/2010 | Striebig et al. | |
| 2010/0139655 A1 | 6/2010 | Genosar et al. | |
| 2010/0313901 A1 | 12/2010 | Fernando et al. | |
| 2011/0030681 A1 | 2/2011 | De Vries et al. | |
| 2011/0126848 A1 | 6/2011 | Zuber et al. | |
| 2011/0192399 A1 | 8/2011 | Wilke et al. | |
| 2011/0226236 A1* | 9/2011 | Buchberger | A24F 40/485 128/200.23 |
| 2012/0304990 A1 † | 12/2012 | Todd | |
| 2012/0325227 A1* | 12/2012 | Robinson | A61M 16/108 131/328 |
| 2013/0032145 A1 | 2/2013 | Adler et al. | |
| 2013/0087144 A1 | 4/2013 | Todd | |
| 2013/0186392 A1 | 7/2013 | Haartsen et al. | |
| 2013/0233309 A1 | 9/2013 | Todd | |
| 2013/0233312 A1 | 9/2013 | Cohn | |
| 2013/0255702 A1 | 10/2013 | Griffith, Jr. et al. | |
| 2013/0276799 A1 | 10/2013 | Davidson et al. | |
| 2014/0041655 A1 | 2/2014 | Barron et al. | |
| 2014/0060554 A1 | 3/2014 | Collett et al. | |
| 2014/0186015 A1 | 7/2014 | Breiwa, III et al. | |
| 2014/0196732 A1* | 7/2014 | Liu | A24F 40/40 131/329 |
| 2014/0217197 A1 | 8/2014 | Selby et al. | |
| 2014/0238423 A1* | 8/2014 | Tucker | A24F 40/46 131/328 |
| 2014/0299141 A1 | 10/2014 | Flick | |
| 2014/0321837 A1 | 10/2014 | Flick | |
| 2014/0345606 A1 | 11/2014 | Talon | |
| 2014/0366609 A1 | 12/2014 | Beck et al. | |
| 2015/0059747 A1 | 3/2015 | Von Schuckmann | |
| 2015/0223521 A1 | 8/2015 | Menting et al. | |
| 2015/0223523 A1 | 8/2015 | McCullough | |
| 2016/0021932 A1 | 1/2016 | Silverstrini et al. | |
| 2016/0051464 A1* | 2/2016 | Trzecieski | A61M 11/003 392/386 |
| 2016/0057811 A1 | 2/2016 | Alarcon et al. | |
| 2016/0235122 A1 | 8/2016 | Krietzman | |
| 2016/0295922 A1 | 10/2016 | John et al. | |
| 2016/0331913 A1 | 11/2016 | Bourque | |
| 2016/0338410 A1* | 11/2016 | Batista | A61M 11/042 |
| 2016/0345630 A1* | 12/2016 | Mironov | B32B 27/06 |
| 2017/0042228 A1* | 2/2017 | Liu | A24F 40/50 |
| 2017/0071251 A1 | 3/2017 | Goch | |
| 2017/0095624 A1* | 4/2017 | Davidson | H05B 3/04 |
| 2017/0099877 A1 | 4/2017 | Worm et al. | |
| 2017/0119979 A1 | 5/2017 | Davidson et al. | |
| 2017/0143042 A1* | 5/2017 | Batista | A24F 40/42 |
| 2017/0144827 A1* | 5/2017 | Batista | A24B 15/167 |
| 2017/0164657 A1* | 6/2017 | Batista | H05B 3/34 |
| 2017/0196262 A1 | 7/2017 | Brereton et al. | |
| 2018/0104214 A1 | 4/2018 | Raichman | |
| 2018/0361334 A1 | 12/2018 | Bahabri | |
| 2019/0117915 A1 | 4/2019 | Raichman | |
| 2019/0224430 A1 | 7/2019 | Raichman | |
| 2020/0229509 A1 | 7/2020 | Griscik et al. | |

FOREIGN PATENT DOCUMENTS

| | | |
|---|---|---|
| CA | 2953074 A1 | 1/2016 |
| CN | 103945716 A | 7/2014 |
| CN | 103974640 A | 8/2014 |
| CN | 203986136 U | 12/2014 |
| CN | 104349687 A | 2/2015 |
| EP | 0525720 A1 | 2/1993 |
| EP | 1007124 A1 | 6/2000 |
| EP | 1029451 A1 | 8/2000 |
| EP | 1385595 A2 | 2/2004 |
| EP | 1504768 A1 | 2/2005 |
| EP | 14178627 | 7/2014 |
| KR | 101319228 | 10/2013 |
| RU | 2536115 C2 | 12/2014 |

(56) References Cited

FOREIGN PATENT DOCUMENTS

| WO | WO-94/09842 A1 | 5/1994 |
|----|----------------|--------|
| WO | WO-2003/037306 A2 | 5/2003 |
| WO | WO-2014/127446 A1 | 8/2014 |
| WO | WO-2015/116934 A1 | 8/2015 |
| WO | WO-2016/001921 A2 | 1/2016 |
| WO | WO-2016/001922 A1 | 1/2016 |
| WO | WO-2016/001923 A2 | 1/2016 |
| WO | WO-2016/001924 A2 | 1/2016 |
| WO | WO-2016/001925 A1 | 1/2016 |
| WO | WO-2016/001926 A1 | 1/2016 |
| WO | WO-2016/026219 A1 | 2/2016 |

OTHER PUBLICATIONS

European Search Report for corresponding European Application No. 16764346.9 dated Aug. 27, 2018.
Search Report and Written Opinion for corresponding Application No. 11201707526U dated Jul. 30, 2018.
An Invitation to pay additional fees dated Jun. 28, 2016 which issued during the prosecution of Applicant's PCT/IL2016/050293.
An International Search Report and a Written Opinion both dated Jul. 31, 2016, which issued during the prosecution of Applicant's PCT/IL2016/050293.
Crafty Vaporizer manual (2014).
Office Action for corresponding Russian Application No. 2017132703 dated Jul. 9, 2019 and English translation thereof.
Office Action for corresponding U.S. Appl. No. 15/559,308 dated Sep. 19, 2019.
Australian Examination Report dated Nov. 1, 2019 for corresponding Australian Application No. 2016231790.
Third Party Submission filed in U.S. Appl. No. 16/227,026 on Sep. 11, 2019.
Japanese Office Action dated Jan. 14, 2020 for corresponding Japanese Application No. 2017-549079.
Office Action for corresponding U.S. Appl. No. 15/559,308 dated Feb. 5, 2020.
Notice of Allowance for U.S. Appl. No. 16/372,816 dated Mar. 26, 2021.
Notice of Allowance for U.S. Appl. No. 16/227,026 dated Mar. 24, 2021.
Office Action for Brazilian Application No. BR112017019916-5 dated May 12, 2020 and English translation.
Notice of Allowance for U.S. Appl. No. 15/559,308 dated May 13, 2020.
Examination Report dated Dec. 1, 2020, issued in corresponding Indian Patent Application No. 201717034587.
Office Action for Japanese Application No. 2017-549079 dated Mar. 22, 2022 and English translation.
Office Action for Indian Application No. 202118024214 dated Mar. 8, 2022.
Office Action dated Jun. 9, 2022 issued in corresponding Canadian patent application No. 2,980,260.
Chinese Office Action dated Feb. 25, 2020 for corresponding Chinese Application No. 201680022671.5.
Office Action for Philippines Application No. 1-2017-501698 dated Jun. 2, 2020.
Office action dated Dec. 11, 2020, issued in corresponding U.S. Appl. No. 16/372,816.
Office action dated Dec. 11, 2020, issued in corresponding U.S. Appl. No. 16/227,026.
Australian Examination Report dated Sep. 3, 2021 for corresponding Australian Application No. 2021200615.
Office Action for European Application No. 16 764 346.9 dated Oct. 22, 2020.
Office Action for Israeli Application No. 254353 dated Jul. 28, 2020 and English translation.
Office Action for corresponding Japanese Application No. 2017-549079 dated Jul. 7, 2020 and English translation.
Office Action for corresponding Chinese Application No. 201680022671.5 dated Sep. 21, 2020 and English translation.
Examination Report dated Apr. 28, 2022 issued in corresponding European patent application No. 16764346.9.
Office Action for U.S. Appl. No. 16/800,319 dated Jun. 27, 2022.
Office Action for Chinese Application No. 202110468811.4 dated Jul. 8, 2022 and English translation.
Notice of Allowance for U.S. Appl. No. 16/851,804 dated Jul. 25, 2022.
Office Action for Japanese Application No. 2021-147504 dated Aug. 2, 2022 and English translation.
CA Office Action for U.S. Appl. No. 16/851,791 dated Sep. 6, 2022.
Notice of Allowance for U.S. Appl. No. 16/800,319 dated Oct. 13, 2022.
Notice of Allowance dated Nov. 9, 2022 issued in related U.S. Appl. No. 16/851,804.
Office Action dated Dec. 14, 2022 issued in related Korean patent application No. 10-2017-7030137.
Office Action dated Dec. 23, 2022 issued in related U.S. Appl. No. 16/851,791.
Notice of Allowance dated Feb. 23, 2023 issued in related U.S. Appl. No. 16/851,804.
Notice of Allowance dated Mar. 15, 2023 issued in related U.S. Appl. No. 16/800,319.
Decision of Rejection dated March 18, 2023 issued in related Chinese patent application No. 202110468811.4.

\* cited by examiner
† cited by third party

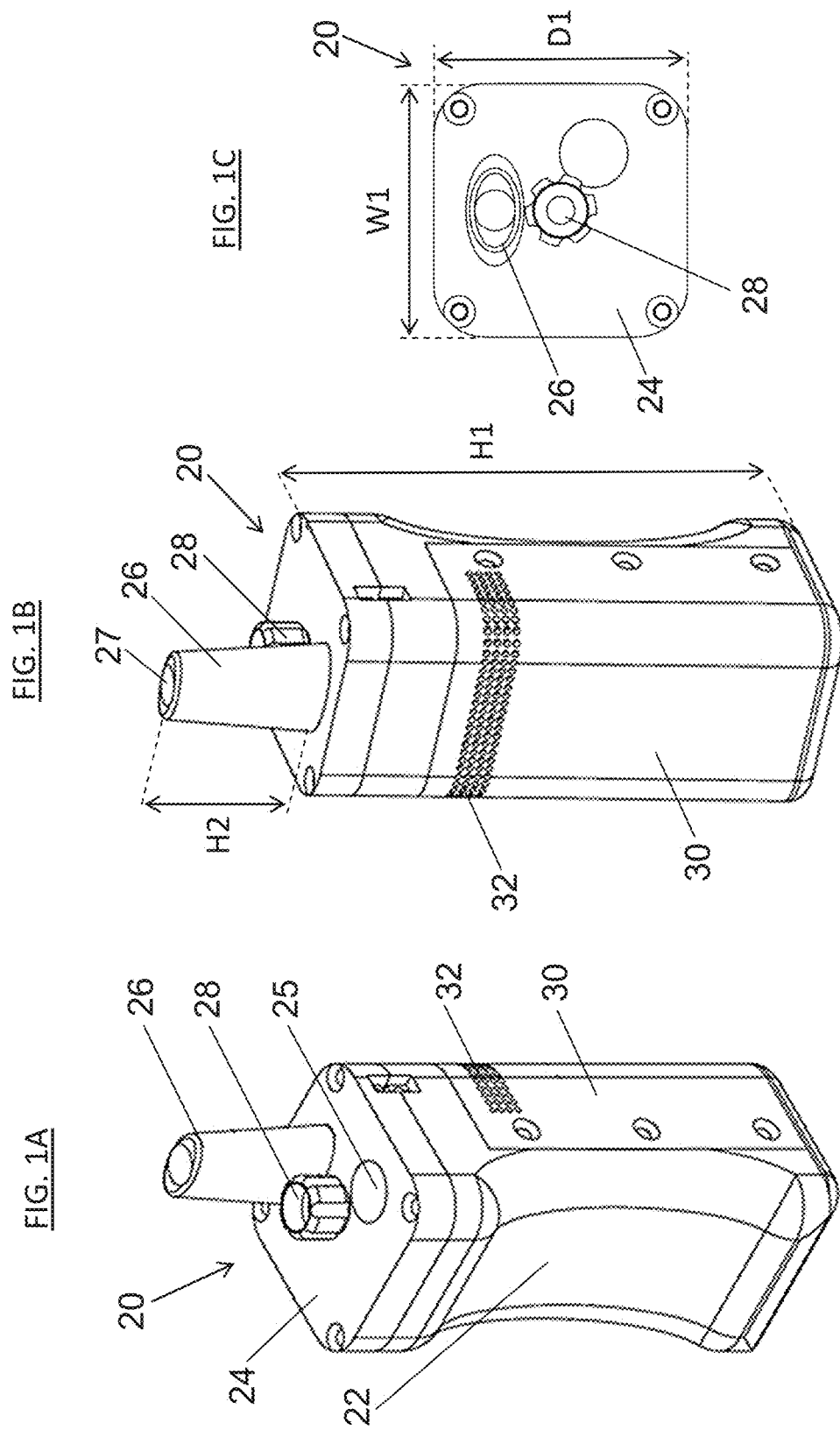

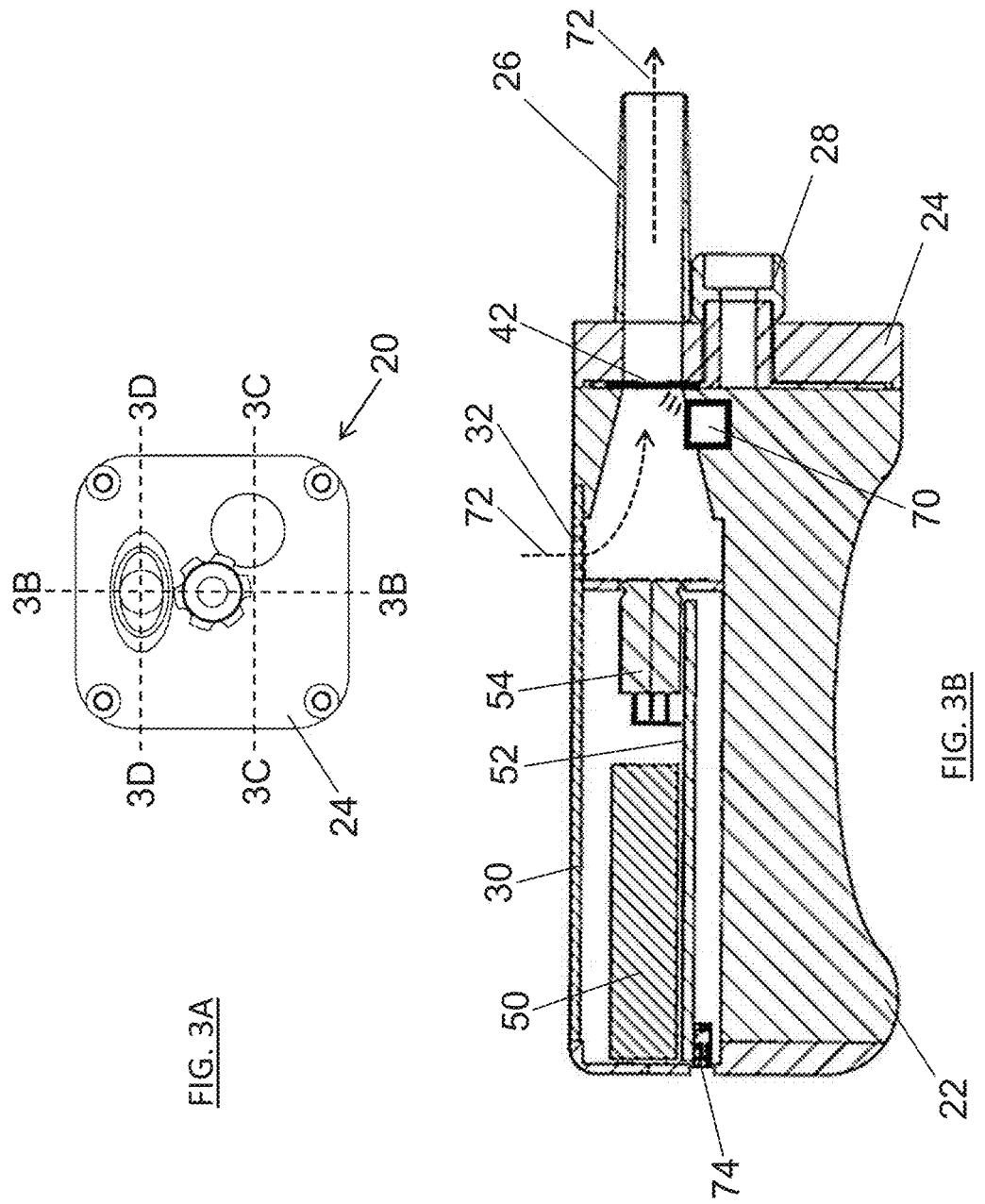

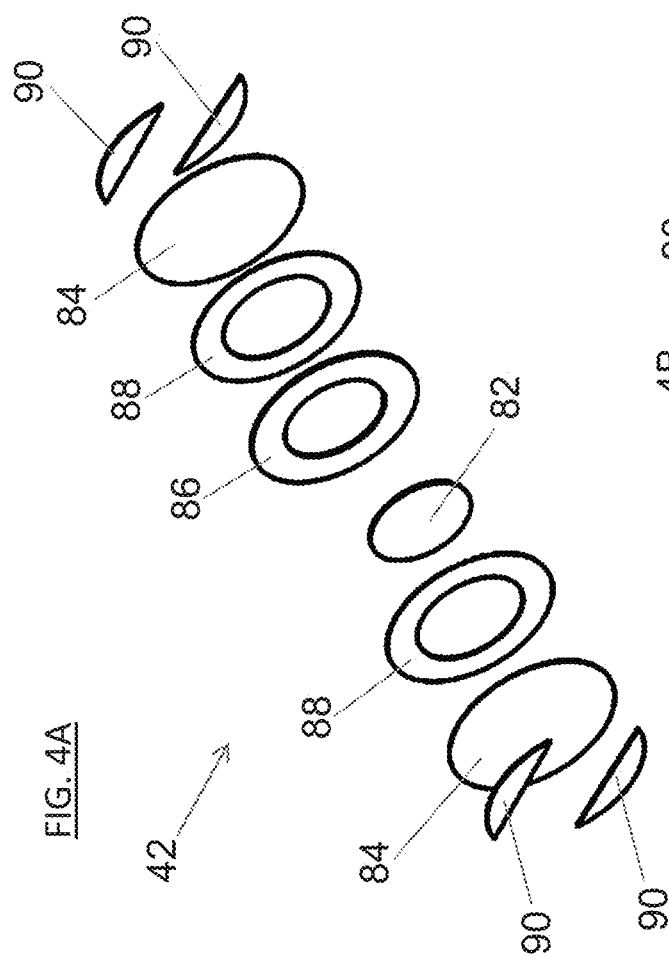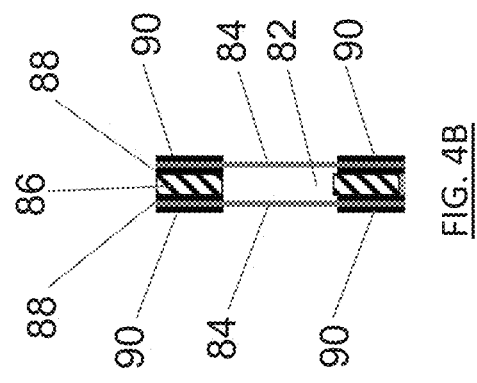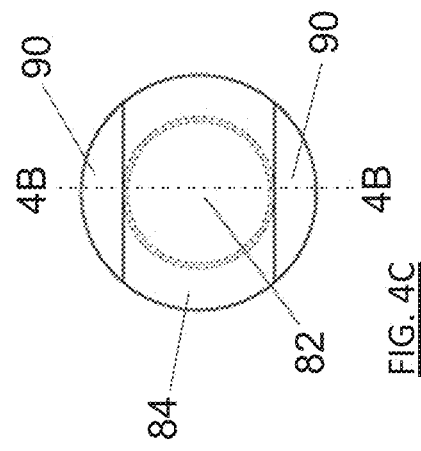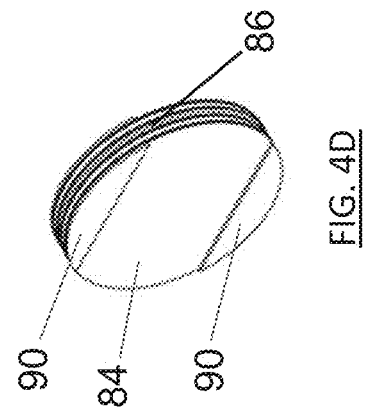

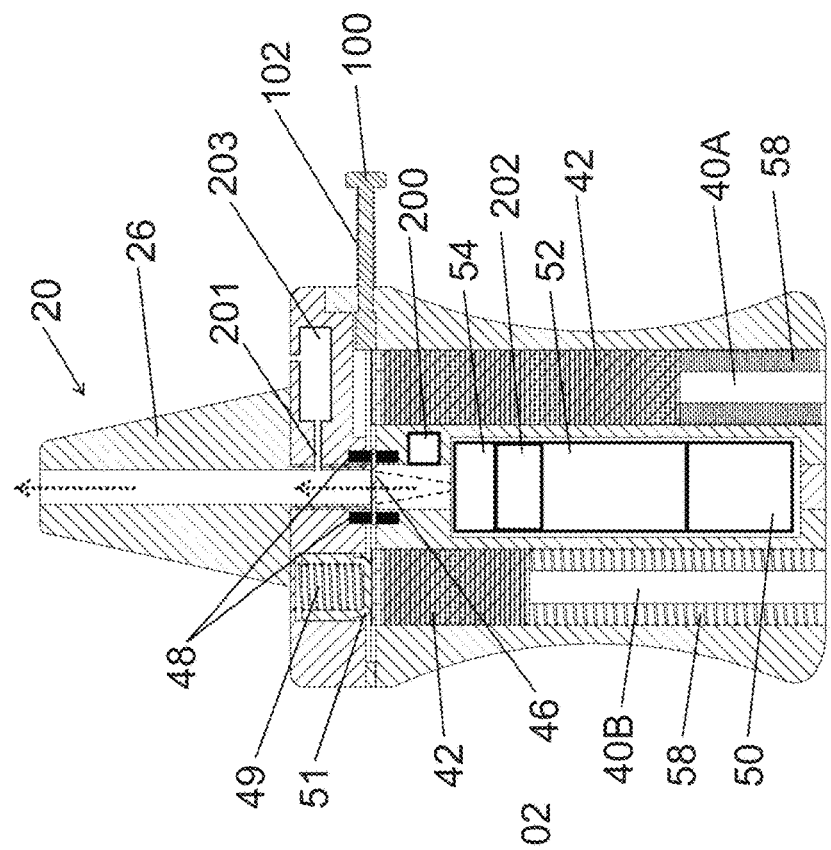
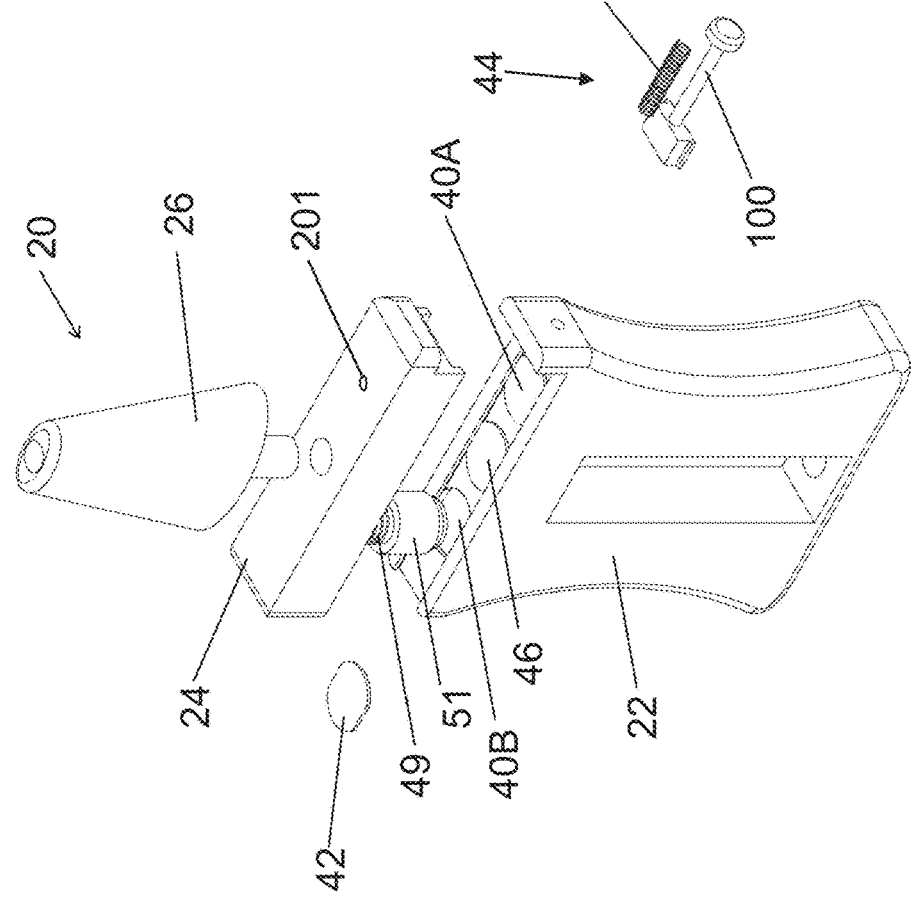

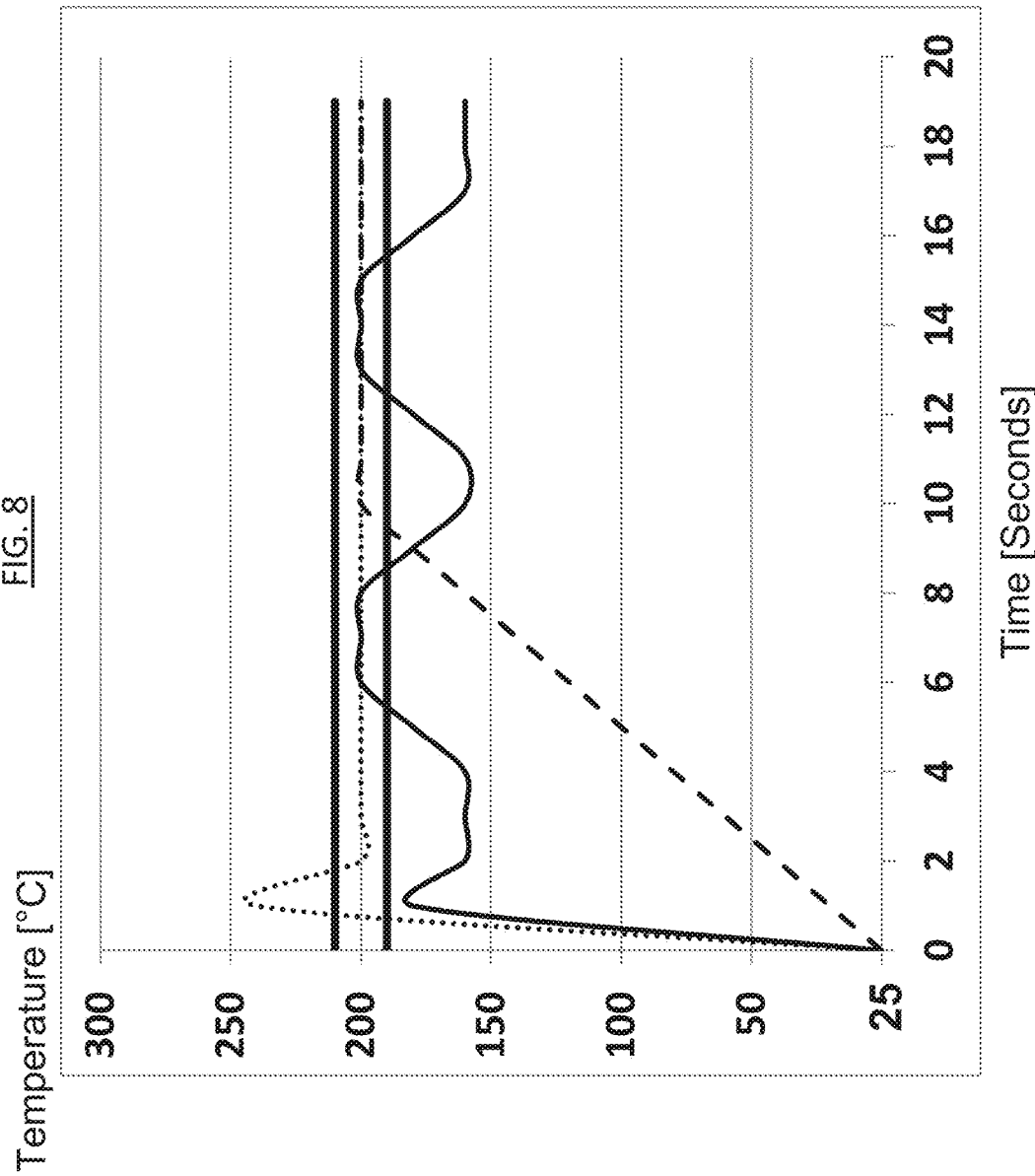

VAPORIZER FOR VAPORIZING A CONSTITUENT OF A PLANT MATERIAL

CROSS-REFERENCE TO RELATED APPLICATIONS

This application is a continuation under 35 U.S.C. § 120 of U.S. application Ser. No. 16/227,026, filed Dec. 20, 2018 which is a divisional under 35 U.S.C. § 121 of U.S. application Ser. No. 14/662,607, filed Mar. 19, 2015, now U.S. Pat. No. 10,179,215, issued Jan. 15, 2019, the entire contents of each of which are incorporated herein by reference.

FIELD

Some applications of the present invention generally relate to medical apparatus. Specifically, some applications of the present invention relate to vaporizers for the delivery of an active ingredient to a subject.

BACKGROUND

Medical use of cannabis and its constituent cannabinoids, such as tetrahydrocannabinol (THC) and cannabidiol (CBD), has a long history. In modern times, cannabis is used by patients suffering from AIDS, or undergoing chemotherapy treatment, in order to relieve nausea and vomiting associated with their conditions. Cannabis is also used in a medicinal manner in order to provide pain relief, to treat muscle spasticity, and to stimulate appetite.

Medicinal cannabis can be administered using a variety of methods, including vaporizing or smoking dried buds, eating extracts, taking capsules or using oral sprays. The legality of medical use of cannabis varies internationally. However, even in countries in which the medical use of cannabis is legal, the provision of cannabis to such users is highly regulated, and it is the case that in almost all Western countries, recreational use of cannabis is illegal.

SUMMARY

In accordance with some applications of the present invention, a vaporizer is used to vaporize the active ingredient of a plant material, by heating the plant material. For example, the vaporizer may be used to vaporize the constituent cannabinoids of cannabis (e.g., tetrahydrocannabinol (THC) and/or cannabidiol (CBD)). Alternatively or additionally, the vaporizer may be used to vaporize tobacco, and/or other plant or chemical substances that contain an active ingredient that becomes vaporized upon the substance being heated.

Typically, the vaporizer houses a plurality of capsules, each of the capsules including a given amount of a plant material that contains an active ingredient. For some applications, the vaporizer is shaped to define first and second receptacles, each of which is shaped to house the plurality of capsules in stacked configurations. While each of the capsules is disposed at a vaporization location within the vaporizer, a heating element causes the active ingredient of the plant material within the capsule to become at least partially vaporized by individually heating the capsule. For some applications, the heating element includes one or more electrodes that heat the capsule via resistive heating, by driving a current into a portion of the capsule (e.g., into a metallic mesh of the capsule), or driving a current into an internal heating element that is housed within the vaporizer. Typically, a capsule-transfer mechanism of the vaporizer individually transfers each of the capsules from the first receptacle to the vaporization location and from the vaporization location to the second receptacle.

For some applications, a two-step heating process is applied to the plant material, as follows. In response to receiving a first input at the vaporizer, a first heating step is initiated. The first heating step is terminated, and further heating of the plant material is withheld, in response to detecting an indication that the temperature of the plant material has reached a first temperature that is typically less than 95 percent of a vaporization temperature of the active ingredient. Subsequently, in response to receiving a second input at the vaporizer (e.g., in response to detecting that a user is inhaling from the vaporizer, or in response to the user pressing a button) the plant material is heated to the vaporization temperature of the active ingredient, in a second heating step.

Typically, the first heating step is performed at a faster heating rate than the second heating step. For some applications, by performing the heating in the two-stage process as described, one or more of the following results are achieved:

1) By withholding the first (rapid) stage of the heating in response to the temperature of the capsule reaching less than 95 percent of the vaporization temperature, even if the heating overshoots, the plant material is not pyrolyzed, since the plant material is not heated to a temperature that is greater than the pyrolysis temperature.

2) Since the second stage of the heating is performed slowly, there is negligible overshooting in the second stage of the heating process, and therefore the plant material does not get pyrolyzed in the second stage of the heating process.

3) Since, during the first stage of the heating, the plant material has already been heated to a temperature that is relatively close the vaporization temperature, even though the second stage of the heating is slow, the time that is required to heat the plant material to the vaporization temperature, from the initiation of the second heating stage, is relatively short (e.g., less than two seconds).

4) Due to low heat conduction of the plant material, if the plant material is heated rapidly, this can give rise to non-uniform heating of the plant material. This can cause some portions of the plant material to be pyrolyzed, and/or other portions of the plant material not to be vaporized. By withholding further heating of the plant material after the first temperature has been reached, and until the second input is received, heat is able to dissipate through the plant material (during the interim period between the first and second heating stages) before any portion of the plant material has been heated to the vaporization temperature. Furthermore, since the temperature increase during the second stage is relatively small, the temperature increase is able to dissipate through the plant material relatively quickly. Thus, relatively uniform heating of the plant material is achieved, such that most of the active ingredient within the plant material is vaporized, while there is substantially no pyrolysis of the plant material.

There is therefore provided, in accordance with some applications of the present invention, a method for use with a vaporizer that vaporizes at least one active ingredient of a plant material, the method including:

receiving a first input at the vaporizer;

in response to receiving the first input, heating of the plant material, in a first heating step;

detecting an indication of a temperature of the plant material;

in response to detecting an indication that the temperature of the plant material is at a first temperature, terminating the first heating step, by withholding causing further temperature increase of the plant material, the first temperature being less than 95 percent of a vaporization temperature of the active ingredient;

subsequently, receiving a second input at the vaporizer; and in response to receiving the second input, heating the plant material to the vaporization temperature of the active ingredient, in a second heating step.

For some applications, detecting the indication of the temperature of the plant material includes detecting the indication of the temperature of the plant material using an optical temperature sensor.

For some applications, the method further includes generating an indication that the first heating step has terminated.

For some applications, terminating the first heating step, by withholding causing further temperature increase of the plant material includes preventing pyrolysis of the active ingredient.

For some applications, the method further includes, subsequent to the second heating step, in response to detecting that no air has been inhaled from the vaporizer for a given time period, reducing a temperature of the plant material to below the vaporization temperature of the plant material.

For some applications, the method further includes detecting a rate of air flow through the vaporizer by detecting an indication of an amount of energy required to maintain the temperature of the plant material constant.

For some applications, heating the plant material in the first heating step includes heating the plant material at a first heating rate, heating the plant material in the second heating step includes heating the plant material at a second heating rate, and the first heating rate is greater than the second heating rate.

For some applications, heating the plant material at the second heating rate includes heating the plant material at a rate of less than 50 degrees Celsius per second.

For some applications, heating the plant material at the rate of less than 50 degrees Celsius per second includes preventing pyrolysis of the active ingredient.

For some applications, heating the plant material at the first heating rate includes heating the plant material at a rate of more than 50 degrees Celsius per second.

For some applications, heating the plant material at the first heating rate includes heating the plant material at a rate of more than 100 degrees Celsius per second.

For some applications, heating the plant material at the first heating rate includes heating the plant material at a rate of more than 50 degrees Celsius per second.

For some applications, heating the plant material at the first heating rate includes heating the plant material at a rate of more than 100 degrees Celsius per second.

For some applications, receiving the second input includes detecting that a user is inhaling from the vaporizer.

For some applications, detecting that the user is inhaling from the vaporizer includes detecting the indication of the temperature of the plant material.

For some applications, detecting that the user is inhaling from the vaporizer includes detecting an indication of an amount of energy required to maintain the temperature of the plant material constant.

For some applications, the plant material includes cannabis and terminating the first heating step includes withholding causing further temperature increase of the plant material in response to detecting an indication that the temperature of the plant material has reached a temperature that is less than 170 degrees Celsius.

For some applications, terminating the first heating step includes withholding causing further temperature increase of the plant material in response to detecting an indication that the temperature of the plant material has reached a temperature that is less than 160 degrees Celsius.

For some applications, detecting the indication of the temperature of the plant material includes detecting a temperature of a capsule in which the plant material is housed.

For some applications, the capsule includes a metallic mesh, and detecting the temperature of the capsule includes detecting electrical resistance of the mesh.

There is further provided, in accordance with some applications of the present invention, apparatus for use with a plant material that includes at least one active ingredient, the apparatus including:

a vaporizer configured to vaporize the active ingredient of the plant material, the vaporizer including:
   a heating element configured to heat the plant material;
   a temperature sensor configured to detect an indication of a temperature of the plant material; and
   control circuitry configured to:
     receive a first input;
     in response to receiving the first input, drive the heating element to heat the plant material at a first heating rate, in a first heating step;
     in response to receiving, from the temperature sensor, an indication that the temperature of the plant material is at a first temperature, terminate the first heating step, by withholding causing further temperature increase of the plant material by the heating element, the first temperature being less than 95 percent of a vaporization temperature of the active ingredient;
     subsequently, receive a second input at the vaporizer; and
     in response to receiving the second input, drive the heating element to heat the plant material to the vaporization temperature of the active ingredient at a second heating rate that is less than the first heating rate, in a second heating step.

For some applications, the control circuitry is configured to be removed from the vaporizer and to be coupled to a second vaporizer.

For some applications, the apparatus further includes a phase-change material that is coupled to the capsule, the phase-change material being configured to undergo a phase change at a temperature that is below a pyrolysis temperature of the plant material.

For some applications, the capsule includes at least one hollow wire, and the phase-change material is housed inside the hollow wire.

There is further provided, in accordance with some applications of the present invention, apparatus including:

a vaporizer shaped to define at least first and second receptacles, the vaporizer including:
   a plurality of capsules, each of the capsules including a plant material that contains an active ingredient, the first and second receptacles each being shaped to house the plurality of capsules in stacked configurations;
   a heating element configured, while each of the capsules is disposed at a vaporization location within the vaporizer, to cause the active ingredient of the plant material within the capsule to become at least partially vaporized by individually heating the capsule; and a capsule-transfer mechanism configured to individually transfer each of the capsules from the first receptacle to the vaporization location and from the vaporization location to the second receptacle.

For some applications, the capsule-transfer mechanism includes a rotating capsule-transfer mechanism, configured to transfer the capsules by rotating.

For some applications, the first and second receptacles and the vaporization location are linearly aligned with each other, and the capsule-transfer mechanism includes a linear capsule-transfer mechanism, configured to move each of the capsules by moving linearly.

For some applications, the heating element includes one or more electrodes configured to heat the capsules via resistive heating, by driving an electrical current into the portion of the capsule.

For some applications, each of the capsules includes one or more metallic meshes, and the one or more electrodes are configured to heat the capsules by driving the electrical current into the one or more metallic meshes of the capsule.

For some applications, a width of the vaporizer is less than 9 cm. For some applications, a depth of the vaporizer is less than 6 cm. For some applications, a height of the vaporizer is less than 20 cm.

There is further provided, in accordance with some applications of the present invention, a method including:

providing a vaporizer shaped to define at least first and second receptacles, a plurality of capsules being housed in a stacked configuration inside the first receptacle, and each of the capsules including a plant material that contains an active ingredient;

using a capsule-transfer mechanism individually transferring a first one of the capsules from the first receptacle to a vaporization location within the vaporizer;

when the first capsule is disposed at the vaporization location within the vaporizer, causing the active ingredient within the plant material within the first capsule to become at least partially vaporized by individually heating the capsule; and using the capsule-transfer mechanism individually transferring the first capsule from vaporization location to the second receptacle, the second receptacle being configured to house a plurality of the capsules in a stacked configuration.

There is further provided, in accordance with some applications of the present invention, apparatus including:

a vaporizer including:
at least one capsule including:
upper and lower meshes; and
a given amount of a plant material housed between the upper and lower meshes, the plant material containing at least one active ingredient;
control circuitry; and
first, second, third and fourth electrodes,
the control circuitry being configured to vaporize the at least one active ingredient of the plant material by:
driving a current from the first electrode to the second electrode via the lower mesh, and
driving a current from the third electrode to the fourth electrode via the upper mesh.

There is additionally provided, in accordance with some applications of the present invention, a method including:
providing a capsule that includes upper and lower meshes, and a given amount of a plant material housed between the upper and lower meshes, the plant material containing at least one active ingredient; and
vaporizing the at least one active ingredient of the plant material by:
driving a current from a first electrode to a second electrode via the lower mesh, and
driving a current from a third electrode to a fourth electrode via the upper mesh.

There is further provided, in accordance with some applications of the present invention, apparatus including:
a vaporizer including:
at least one capsule, the capsule including a plant material that contains at least one active ingredient;
a heating element configured, to cause the active ingredient within the plant material within the capsule to become at least partially vaporized by heating the capsule; and
a vibrator configured to vibrate the capsule.

For some applications, the vibrator includes a vibrator selected from the group consisting of: a vibration motor, a piezo-electric crystal, a sonic vibrator, and an ultrasonic vibrator.

For some applications, the vibrator is configured to increase airflow through the capsule by vibrating the capsule.

For some applications, the vibrator is configured to mix the plant material within the capsule by vibrating the capsule.

For some applications, the vibrator is configured to increase a uniformity of heating of the plant material within the capsule by vibrating the capsule.

There is additionally provided, in accordance with some applications of the present invention, a method including:
providing a vaporizer that includes at least one capsule, the capsule including a plant material that contains at least one active ingredient;
activating a heating element within the vaporizer to cause the active ingredient within the plant material to become at least partially vaporized by heating the capsule; and
activating a vibrator within the vaporizer to vibrate the capsule.

The present invention will be more fully understood from the following detailed description of embodiments thereof, taken together with the drawings, in which:

BRIEF DESCRIPTION OF THE DRAWINGS

FIGS. 1A-C are schematic illustrations of respective views of the exterior of a vaporizer, in accordance with some applications of the present invention;

FIG. 3A is a top view and FIGS. 3B-D are respective cross-sectional views of the vaporizer of FIGS. 1A-C, in accordance with some applications of the present invention;

FIGS. 4A-D are schematic illustrations of respective views of a capsule that contains plant material that includes an active ingredient, in accordance with some applications of the present invention;

FIGS. 7A-B are schematic illustration of respective views of a vaporizer that includes a linear capsule-transfer mechanism, in accordance with some applications of the present invention; and FIG. 8 is a graph illustrating a technique for heating plant material using a vaporizer, in accordance with some applications of the present invention.

DETAILED DESCRIPTION

Figure 2A:
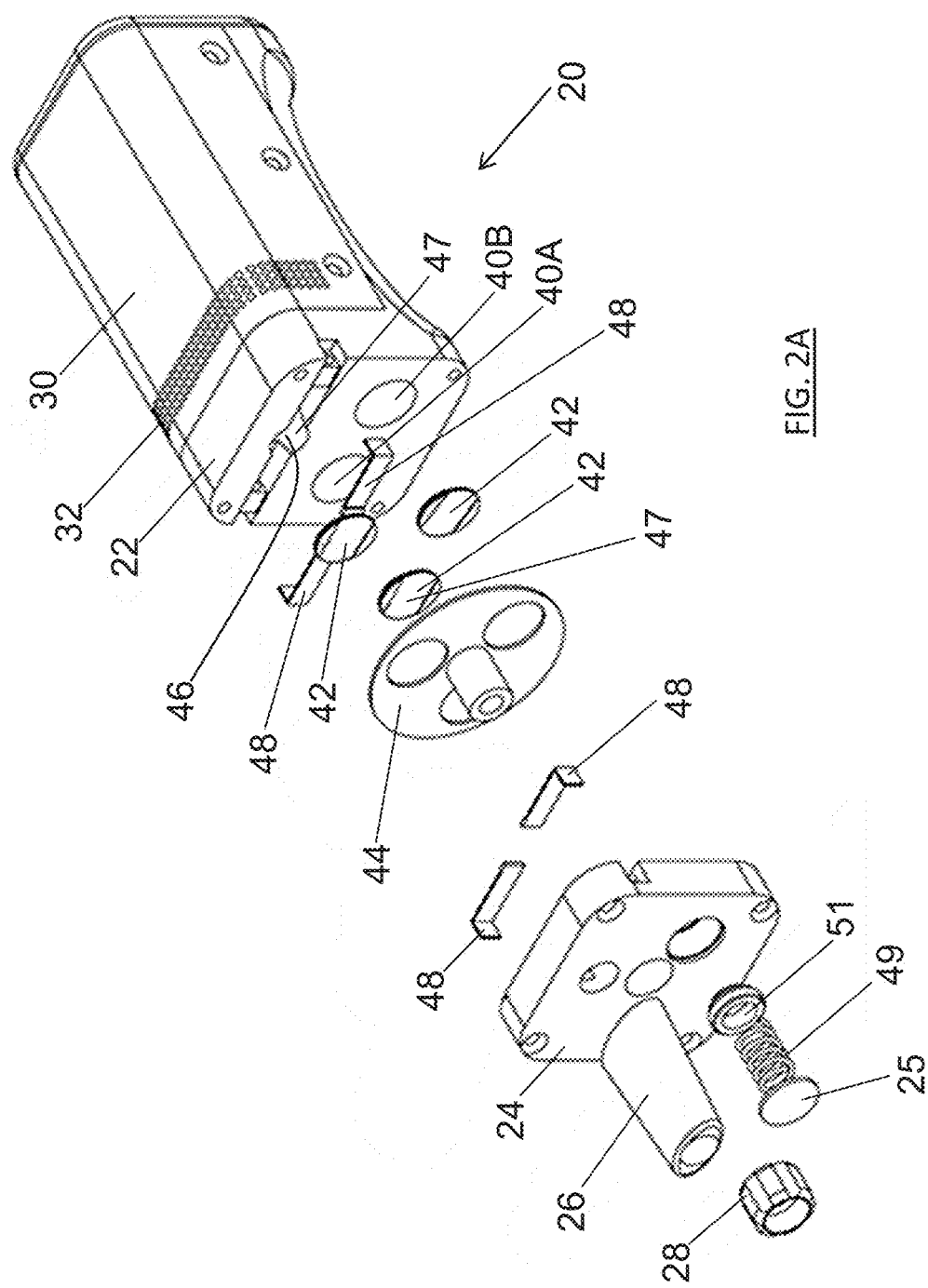
FIGS. 2A-B are exploded views of the vaporizer of FIGS. 1A-C, in accordance with some applications of the present invention.

Reference is now made to FIGS. 1A-C, which are schematic illustrations of respective views of the exterior of a vaporizer 20, in accordance with some applications of the present invention. Typically, vaporizer 20 is used to vaporize the active ingredient of a plant material. For example, vaporizer 20 may be used to vaporize the constituent cannabinoids of cannabis (e.g., tetrahydrocannabinol (THC) and/or cannabidiol (CBD)). Alternatively or additionally, the vaporizer may be used to vaporize tobacco, and/or other plant or chemical substances that contain an active ingredient that becomes vaporized upon the substance being heated.

Vaporizer 20 includes a main body 22, which houses capsules and control circuitry of the vaporizer, as described in further detail hereinbelow. The control circuitry is configured to act as a control unit, which controls the functioning of the vaporizer. Typically, the vaporizer additionally includes a top cover 24, from which a mouthpiece 26 protrudes. During use, the user typically inhales the vaporized active ingredient via the mouthpiece.

Typically, vaporizer 20 is configured to be portable and, during use, the vaporizer is configured to be held in a single hand of a user. The dimensions of the vaporizer are typically as follows:
- A height H1 of main body 22 of the vaporizer (excluding mouthpiece 26) is typically more than 8 cm (e.g., more than 10 cm), and/or less than 15 cm (e.g., less than 12 cm), e.g., between 8 cm and 15 cm, or between 10 and 12 cm.
- A height H2 of mouthpiece 26, is typically more than 2 cm (e.g., more than 2.5 cm), and/or less than 6 cm (e.g., less than 3.5 cm), e.g., between 2 cm and 6 cm, or between 2.5 and 3.5 cm.
- Typically, the total height of the vaporizer, including the mouthpiece is less than 20 cm, e.g., less than 15 cm.
- A width W1 of the vaporizer is typically more than 3 cm (e.g., more than 4 cm), and/or less than 9 cm (e.g., less than 6), e.g., between 3 cm and 9 cm, or between 4 cm and 6 cm.
- A depth D1 of the vaporizer is typically more than 2 cm (e.g., more than 3 cm), and/or less than 6 cm (e.g., less than 5), e.g., between 2 cm and 6 cm, or between 3 cm and 5 cm.

Figure 2B:
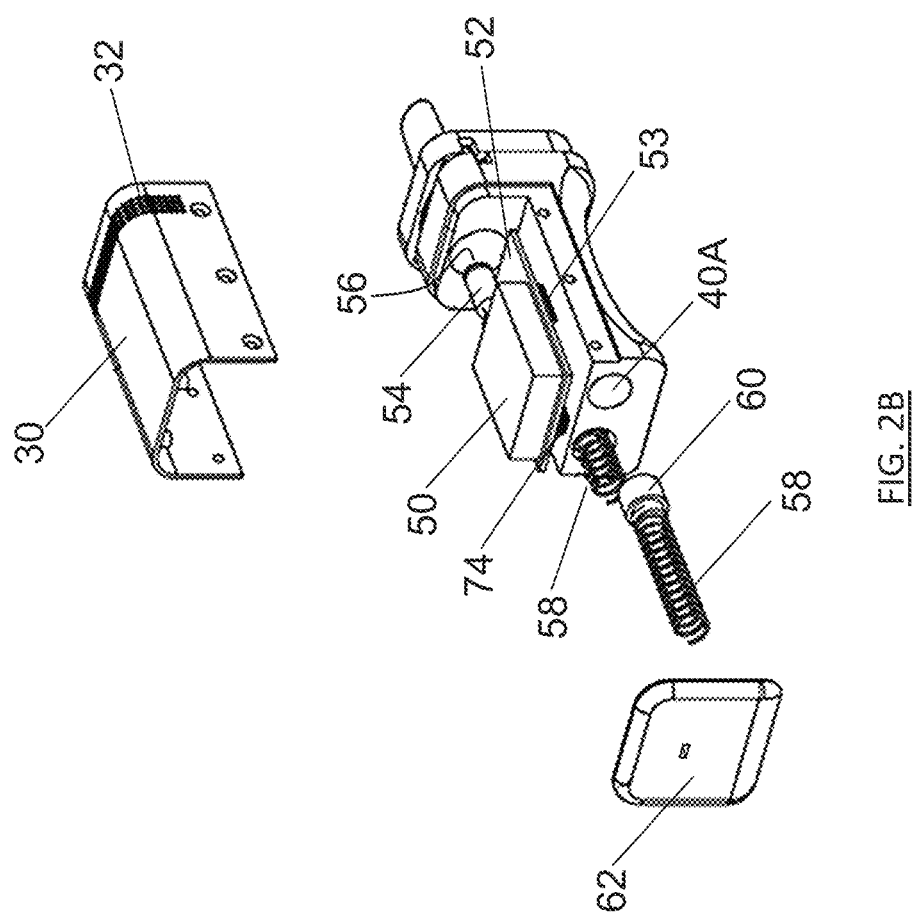

For some applications, a capsule-transfer wheel 28 is disposed on the outside of the top cover. The capsule-transfer wheel controls a capsule-transfer mechanism 44 (FIG. 2A). As described in further detail hereinbelow, the capsule-transfer mechanism is configured to (a) individually transfer unused capsules from a first receptacle 40A (FIG. 2A) within the main body of the vaporizer to a vaporization location 46 (FIG. 2A), at which the capsule is heated such as to vaporize the active ingredient, and (b) to individually transfer used capsules from the vaporization location to a second receptacle 40B (FIG. 2A) within the main body of the vaporizer. For some applications, the capsule-transfer mechanism is a rotatable mechanism, e.g., a rotatable disc, as shown in FIGS. 2A-B. For some such applications, the capsule-transfer wheel is turned by a user in order to control the rotatable capsule-transfer mechanism. Alternatively or additionally, the rotatable capsule-transfer mechanism (or any other capsule-transfer mechanism described herein) is controlled by an electric motor (not shown).

For some applications, a removable back cover 30 is disposed upon main body 22 of vaporizer 20. As shown, for some applications, the back cover defines a grill 32. Grill 32 is configured to allow airflow into the main body of the vaporizer, as described in further detail hereinbelow.

For some applications, the inner surface of mouthpiece (and/or other portions of the vaporizer) includes a lipophobic or hydrophobic coating 27 that is configured to prevent products of the vaporization of the active ingredient from sticking to the inner surface of the mouthpiece. Alternatively or additionally, electrical charge is driven onto surfaces of the vaporizer (such as the inner surface of mouthpiece 26), such that the charge accumulates on the surfaces and repels products of the vaporization of the active ingredient from the surfaces.

Reference is now made to FIGS. 2A-B, which are exploded views of vaporizer 20, in accordance with some applications of the present invention.

Referring to FIG. 2A, typically, vaporizer 20 includes first and second receptacles 40A and 40B, which are configured to house capsules 42, which include a plant material that contains an active ingredient. Unused capsules are typically housed in a stacked configuration inside the first receptacle, and used capsules are housed in a stacked configuration inside the second receptacle.

Capsule-transfer mechanism 44 is configured to transfer the capsules form the first receptacle to the second receptacle. For some applications, the capsule-transfer mechanism is a rotatable capsule-transfer mechanism (e.g., a rotatable disc), as shown in FIG. 2B. Typically, the capsule-transfer mechanism is configured to (a) individually transfer unused capsules from first receptacle 40A to vaporization location 46 at which the capsule is heated such as to vaporize the active ingredient, and (b) to individually transfer used capsules from the vaporization location to second receptacle 40B.

For some such applications, vaporizer 20 includes one or more heating elements, which are configured to heat the plant material within the capsule (such as to vaporize the active ingredient within the plant material). For some applications, electrodes 48 are configured to act as heating elements, by heating the plant material within the capsule, by driving an electrical current into capsule 42. For some applications, capsule 42 includes one or more metallic meshes 84 (FIG. 4A). The electrodes heat the plant material by heating the one or more meshes via resistive heating, by driving a current into the one or more meshes. Alternatively or additionally, the electrodes heat an internal heating element that is housed within the vaporizer, by driving a current into the internal heating element. Typically, the electric current that is driven is fixed, such that, for example, the heating of the capsules is not affected by variations in the degree of contact between the electrodes and the meshes of the capsules.

For some applications, a spring 49 with a pushing element 51 is disposed underneath a portion 25 of top cover 24. The spring is configured to push the used capsules into second receptacle 40B.

For some applications, a portion of capsule 42 is coated or filled with a phase-change material 47. The phase-change material is selected such as to maintain the capsule below the pyrolysis temperature of the plant material, and thereby prevents the plant material from being pyrolyzed. For example, the phase-change material may undergo a solid-to-liquid phase change at a temperature that is between the vaporization temperature and the pyrolysis temperature of the plant material, such that the phase-change material absorbs heat as latent heat of fusion at this temperature. For some applications, a portion of the vaporizer (e.g., vaporization location 46, receptacle 40A and/or receptacle 40B) is coated with phase-change material 47.

Referring now to FIG. 2B, typically, a power supply 50 (e.g., a battery) and control circuitry 52 are housed inside the main body of vaporizer 20. Typically, the power supply and/or the control circuitry are coupled to the main body of the vaporizer by a coupling element 53, such as an adhesive, a screw, a clip, and/or a pin. For some applications, the control circuitry is configured to drive a current into the capsule via electrodes 48, using power supplied by the power supply.

For some applications, back cover 30 is removable and reusable, and control circuitry 52, power supply 50, and/or temperature sensor 54 are coupled to the back cover (e.g., by being housed in the back cover). Typically, for such applications, after all of the capsules in the vaporizer have been vaporized, the back cover is removed, together with the components that are coupled to the back cover. The back cover and the components are then transferred and coupled to a different vaporizer that includes unused capsules.

For some applications, vaporizer 20 includes a temperature sensor 54 that is configured to measure an indication of the temperature of the plant material that is being heated, e.g., by measuring the temperature of the capsule that is being heated. For example, the temperature sensor may be an optical temperature sensor, such as an infrared temperature sensor, that is configured to measure the temperature of the capsule without contacting the capsule. In this manner, the infrared temperature sensor measures the temperature of the capsule, without affecting the temperature of the capsule by drawing heat from the capsule. For some applications, the temperature sensor is covered with a lipophobic or hydrophobic coating 56 that protects the temperature sensor from products of the vaporization being deposited upon the temperature sensor. For some applications, a different temperature sensor is used. For example, the control circuitry may detect the temperature of the capsule by detecting changes in the resistance of components of the capsule (e.g., mesh 84 of the capsule) using electrodes 48.

As described hereinabove, typically unused capsules are housed inside first receptacle 40A and used capsules are housed inside receptacle 40B. Typically, springs 58 and pushing elements 60 are coupled to a bottom cover 62 of the vaporizer. The springs and pushing elements are configured to maintain the stacked configurations of the capsules inside the receptacles by pushing the capsules toward the top of the vaporizer.

Figure 3D:
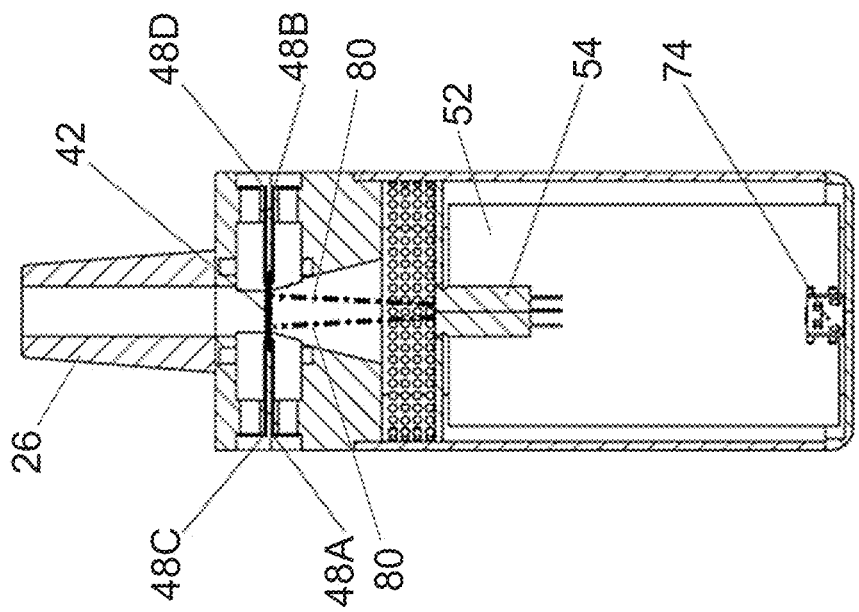
Figure 3C:
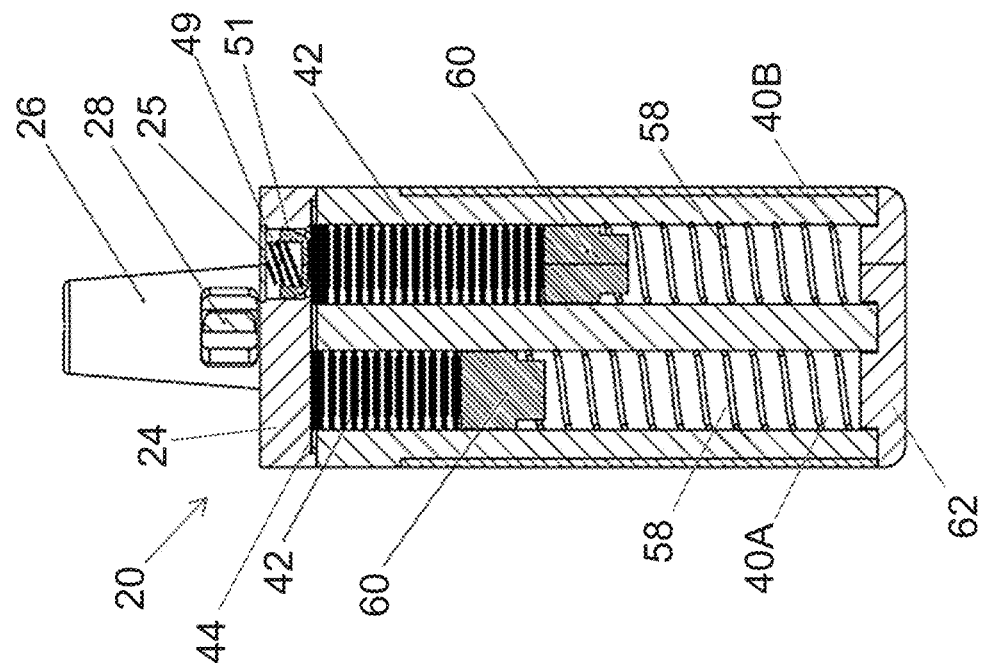

Reference is now made to FIGS. 3A-D. FIGS. 3B-D are schematic cross-sectional views of vaporizer 20, in accordance with some applications of the present invention. FIG. 3A is a top view of vaporizer 20, in accordance with some applications of the present invention. FIG. 3A includes lines indicating the locations of the cross-sections that are shown, respectively, in FIGS. 3B, 3C, and 3D.

Referring to FIG. 3B, for some applications, vaporizer 20 includes a vibrator 70 that is configured to vibrate capsule 42, while the capsule is being heated. During use of the vaporizer, the user inhales via mouthpiece 26. This causes air to flow through grill 32 to the mouthpiece via the capsule, as indicated by airflow arrows 72. Due to the heating of the capsule, the active ingredient within the plant material of the capsule is vaporized and is introduced into the air that is flowing through the vaporizer. For some applications, by vibrating the capsule, the vibrator reduces blockage of air flow through the capsule, and/or increases airflow through the capsule relative to if the capsule were not vibrated. For some applications, due the vibration of the capsule, a greater amount of the active ingredient vaporizes and enters the airflow than if the capsule were not vibrated. Alternatively or additionally, vibration of the capsule improves the distribution of heat across the capsule, and/or mixes the plant material within the capsule.

In accordance with respective application, vibrator 70 includes a vibration motor, a piezo-electric crystal, a sonic vibrator, an ultrasonic vibrator, and/or a different type of vibrator. For some applications, one or more parameters of the vibration applied by the vibrator is varied such as to increase the efficiency of the active ingredient vaporization, to increase airflow through the capsule, to reduce air flow blockage, to improve distribution of heat across the capsule, and/or to mix the plant material within the capsule. For example, the frequency, the amplitude, and/or the direction of the vibration may be varied.

For some applications, vaporizer 20 includes a port 74 via which the vaporizer is connected to an external source of power and/or data input. For example, power supply 50 may be configured to be recharged by connecting the vaporizer to an external power source via port 74. Alternatively or additionally, control circuitry 52 may receive data, e.g., programming instructions, via port 74.

For some applications, a healthcare professional (e.g., a pharmacist or a doctor) may input instructions into the control circuitry that control the heating rate that is applied for a given amount of air flow through the capsule. By controlling the heating rate per unit air flow, the amount of the active ingredient that is vaporized per unit airflow through the vaporizer may be controlled. Alternatively or additionally, the healthcare professional may input instructions into the control circuitry that control the amount of airflow through the vaporizer that is permitted during each use of the vaporizer, and/or the amount of airflow through the vaporizer that is permitted within a given time period (e.g., per hour, or per day). In this manner, the healthcare professional may control the dosage of the active ingredient that the user is able to receive during each use of the vaporizer, and/or within the given time period. For some applications, the control circuitry is configured to automatically determine the rate and/or volume of air flow through the vaporizer, as described in further detail hereinbelow.

Referring now to FIG. 3C, as shown, capsules 42 that are unused (i.e., capsules, the active ingredient of the plant material of which has not been vaporized) are housed, in a stacked configuration (i.e., such that when the vaporizer is in an upright orientation, the capsules are arranged one above the other), inside receptacle 40A. Used capsules are housed, in a stacked configuration, inside receptacle 40B. As described hereinabove, for some applications, springs 58 and pushing elements 60 are coupled to a bottom cover 62 of the vaporizer and are configured to maintain the stacked configurations of the capsules inside the receptacles by pushing the capsules toward the top of the vaporizer. For some applications, by storing the capsules in stacked configurations, dimensions of the width and depth of vaporizer 20 may be such that the vaporizer can be comfortably held by a user (e.g., within a single hand of the user).

Spring 49 and pushing element 51 typically push the used capsules into receptacle 40B, such that the used capsules are maintained below a plane of movement of capsule-transfer mechanism 44. In this manner, capsules that have been placed inside receptacle 40B remain inside receptacle 40B, even when the capsule-transfer mechanism is moved.

For some applications, capsules 42 have circular cross-sections, and receptacles 40A and 40B define cylindrical tubes that house the capsules. Alternatively, capsules 42 may have a different shape, and receptacles 40A and 40B may define hollow spaces that are shaped so as to conform with the shapes of the capsules.

With reference to FIG. 3D, as described hereinabove, for some applications, temperature sensor 54 is an optical temperature sensor, such as an infrared temperature sensor, that is configured to measure the temperature of the capsule without contacting the capsule. FIG. 3D shows sensor 54 receiving beams 80 of optical light from capsule 42, the capsule having been heated. Sensor 54 is configured to measure the temperature of capsule 42, based upon the received light.

As shown in FIG. 3D, for some applications, electrode 48 includes at least four electrodes 48A, 48B, 48C, and 48D. The plant material contained within the capsule is heated by driving a current from first electrode 48A to second electrode 48B via a lower mesh of capsule 42. Alternatively or additionally, plant material contained within the capsule is heated by driving a current from third electrode 48C to fourth electrode 48D via an upper mesh of capsule 42. For some applications, by heating the plant material in the aforementioned manner, the plant material within the capsule is heated more uniformly than if, for example, a monopolar electrode were to drive a current into a location on the upper or lower mesh. For some applications, capsule 42 includes an internal heating element (e.g., an internal mesh (not shown)), as an alternative or in addition to the upper and lower meshes. The internal heating element is configured to be heated in a similar manner to that described with reference to the upper and lower meshes.

Reference is now made to FIGS. 4A-D, which are schematic illustrations of respective views of capsule 42, the capsule containing plant material 82 that includes an active ingredient, in accordance with some applications of the present invention. As described hereinabove, for some applications, the plant material is cannabis, and the active ingredient is the constituent cannabinoids of cannabis (e.g., tetrahydrocannabinol (THC) and/or cannabidiol (CBD)). Alternatively or additionally, the plant material may be tobacco, and/or other plant or chemical substances that contain an active ingredient that becomes vaporized upon the substance being heated.

For some applications, plant material 82 is housed between upper and lower metallic meshes 84. For some applications, each of the meshes has openings of more than 15 micron (e.g., more than 20 micron), and/or less than 80 micron (e.g., less than 50 micron), e.g., 15-60 micron, or 20-50 micron. Typically the meshes are coupled to a central portion 86 of the capsule (e.g., a central disc, as shown), the central portion defining a hole. For example, the meshes may be coupled to the central portion via an adhesive 88, such as a high-temperature-resistant glue, or double-sided adhesive. Typically, the adhesive is configured such that the adhesive does not emit fumes, even when the adhesive is subjected to a high temperature, such as a temperature of greater than 200 degrees Celsius. Typically, the plant material is housed between the meshes and within the hole defined by the central portion of the capsule.

Typically, plant material 82 is ground, such that (a) the plant material is in sufficiently small pieces that the material fits within the capsule, and a large surface area of the plant material is exposed to air flow through the vaporizer (b) the pieces of the plant material are sufficiently large that they do not pass through the meshes, and (c) the active ingredient retains its potency. For some applications, the plant material is cryogenically ground and/or powderized, e.g., using techniques that are known in the art.

For some applications, spacing elements 90 are coupled to the outside of one or both of the meshes. The spacing elements are configured such that, when the capsules are disposed in the stacked configuration inside the vaporizer, there is a space between the upper mesh of a capsule and the lower mesh of the adjacent capsule. The spacing elements are shaped such as to perform the aforementioned function without blocking airflow through the meshes and/or the plant material, and without interfering with the contact between electrodes 48 and meshes 84. For some applications, the spacing element is a single sided adhesive tape. For some applications, an anti-adhesive coating material is used as the spacing element. The anti-adhesive coating material is configured to prevent the unused capsules from becoming stuck to one another when the unused capsules are housed in receptacle 40A.

For some applications, central portion 86 of capsule 42 is made of a material that has a high heat capacity and/or low heat conductivity so that it reduces heat loss from the capsule to the surrounding area and reduces heating of the surrounding area during evaporation process. For some applications, at least one of the wires of meshes 84 is hollow, and a phase-change material is disposed inside the hollow wire. The phase-change material reduces heat loss from the capsule, by causing the capsule to preferentially absorb heat relative to the areas surrounding the capsule. Alternatively or additionally, a phase change material is coupled to the capsule is a different manner, e.g., by coating the capsule. As described hereinabove, typically, the phase-change material is selected such as to maintain the capsule below the pyrolysis temperature of the plant material, and to thereby prevent the plant material from being pyrolyzed.

Figure 5:
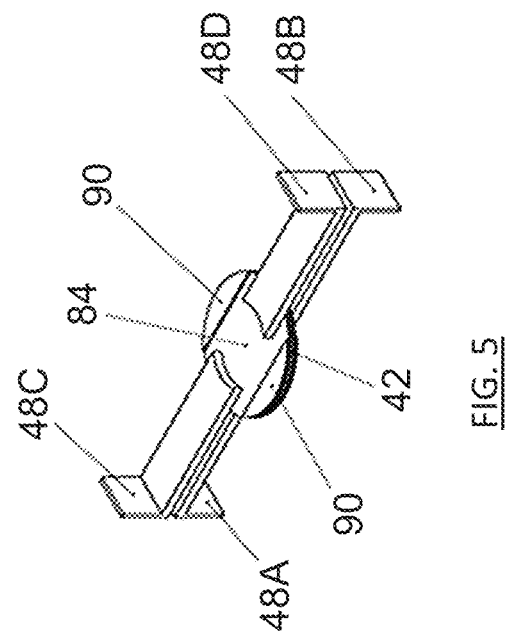
FIG. 5 is a schematic illustration of electrodes of the vaporizer in contact with a mesh of a capsule that contains plant material that includes an active ingredient, in accordance with some applications of the present invention.

Reference is now made to FIG. 5, which is a schematic illustration of electrodes 48 of vaporizer 20 in contact with meshes 84 of capsule 42, in accordance with some applications of the present invention. As shown, electrodes contact the meshes even when spacing elements 90 are disposed upon the outsides of the meshes.

Figure 6C:
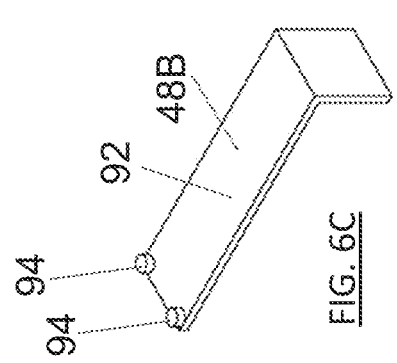
FIGS. 6A-D are schematic illustrations of respective configurations of the electrodes of the vaporizer, in accordance with some applications of the present invention.
Figure 6D:
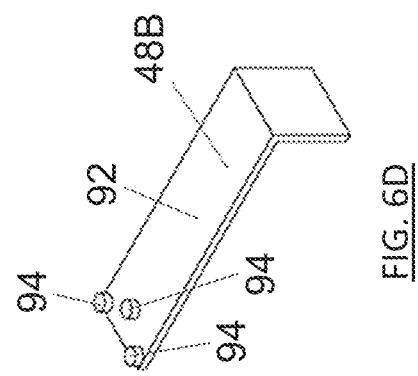
Figure 6A:
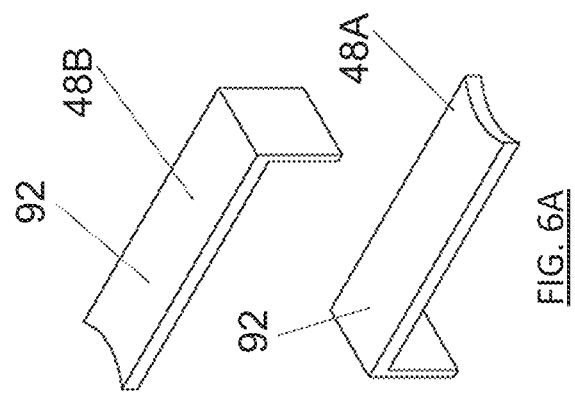
Figure 6B:
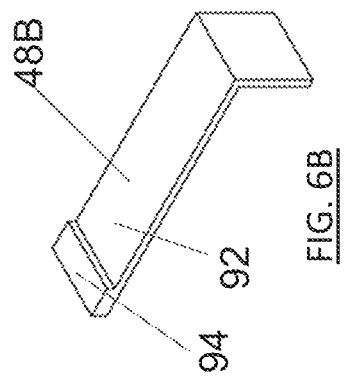

Reference is now made to FIGS. 6A-D, which are schematic illustrations of respective configurations of electrodes 48 of vaporizer 20, in accordance with some applications of the present invention. FIG. 6A shows examples of electrodes 48A and 48B, in accordance with some applications of the present invention. As shown, for some applications, a surface 92 of the electrode acts as an electrical contact, via which electrical contact is made with a mesh of the capsule. FIGS. 6B-D show examples of electrode 48B, in accordance with respective applications of the present invention. For some applications, the electrodes include contacts 94 that protrude from surface 92 of the electrode. As shown, the contact may be shaped as a flat plate (FIG. 6B), or as a plurality of points, e.g., two points (FIG. 6C), or three points (FIG. 3D).

Reference is now made to FIGS. 7A-B, which are schematic illustrations of respective views of vaporizer 20, capsule-transfer mechanism 44 of the vaporizer being a linear mechanism, in accordance with some applications of the present invention.

As shown in FIGS. 7A-B, in accordance with some applications, capsules 42 are shaped in a shape that is not circular. For example, as shown in FIGS. 7A-B, the capsule may have a racetrack-shaped cross section. For such applications, receptacles 40A and 40B define hollow spaces that are shaped so as to conform with the shape of the capsules.

For some applications, the top of receptacle 40A, the top of receptacle 40B, and the vaporization location, at which the capsules are heated, are aligned with each other (for example, across the width of the vaporizer, as shown in FIGS. 7A-B). A linear capsule-transfer mechanism 44 is configured to push unused capsules from receptacle 40A to vaporization location 46 at which the capsule is heated, and from the vaporization location to second receptacle 40B. For some applications, the linear capsule-transfer mechanism includes a pusher 100 that is configured to transfer the capsules in the manner described above, by the pusher being pushed axially in a given direction. For some applications, a spring 102 is coupled to the pusher, the spring being configured to apply a force to the pusher that opposes movement of the pusher in the given direction.

With reference to FIG. 7B, for some applications, a pump 200 (shown schematically in FIG. 7B) is used to control air flow through the vaporizer. For some applications, the vaporizer is shaped to define a supplementary airflow channel 201, which provides airflow out of the mouthpiece, but not via the capsule that is being vaporized. In this manner, in response to a large inhalation by the user, the vaporizer is able to provide air to the user, without increasing the dosage of the active ingredient that is provided to the user. For some applications, a valve 203 (shown schematically in FIG. 7B) is disposed within the supplementary airflow channel and is configured to control airflow through the supplementary airflow channel.

For some applications, vaporizer 20 includes an airflow sensor, e.g., a valve 202(shown schematically in FIG. 7B). The valve is configured to measure airflow through the vaporizer. For some applications, the measured airflow is received as an input to the control circuitry, and the control circuitry varies a parameter of the heating in response to the detected airflow.

Apart from the differences described in the above paragraphs, vaporizer 20 and portions thereof shown in FIGS. 7A-B are generally similar to the vaporizer and portions thereof described with reference to FIGS. 1A-6D. The scope of the present invention includes combining features of the vaporizer and portions thereof described with reference to FIGS. 7A-B, with features of the vaporizer and portions thereof described with reference to FIGS. 1A-6D, and vice versa.

Reference is now made to FIG. 8, which is a graph illustrating respective techniques for heating plant material using a vaporizer, such as vaporizer 20, in accordance with some applications of the present invention. The x-axis of the graph indicates time (measured in seconds), and the y-axis indicates the temperature (measured in degrees Celsius) of a capsule that contains a plant material (and therefore indicates the temperature of the plant material within the capsule), as described herein.

As described hereinabove, for some applications, vaporizer 20 is used to vaporize active ingredients within cannabis. Cannabis typically has a vaporization temperature of 180 degrees Celsius, and begins to become pyrolyzed at 220 degrees Celsius. Therefore, it is typically desirable to heat the cannabis to a temperature of between 190 degrees Celsius and 210 degrees Celsius. The upper and lower boundaries of the desired temperature range to which to heat cannabis are denoted on the graph of FIG. 8, by the two solid horizontal lines at 190 degrees Celsius and 210 degrees Celsius. Further typically, it is desirable not to heat the cannabis to a temperature that is greater than the described temperature, in order to prevent pyrolysis of the cannabis. Typically, when the vaporizer is used with plant materials other than cannabis, similar considerations are applicable, although the desired temperature to which the plant material should be heated will vary depending on the characteristics of the plant material that is being used with the vaporizer.

One possible way of heating the plant material to the desired temperature is via gradual heating, as denoted by the dashed diagonal line, which shows the plant material being heated to the desired temperature over a period of more than 12 seconds. Another possible way to heat the plant material is via rapid heating, as denoted by the dotted curve in FIG. 8. Typically, if the plant material is heated rapidly, then initially there is an overshoot in the temperature to which the plant material is heated. For example, this may be because there is a time lag between when the plant material reaches the desired temperature and when the control circuitry detects that the desired temperature has been reached and withholds causing further temperature increase of the plant material in response to the detected temperature. This is indicated in FIG. 8, which shows that the dotted curve initially rises above 220 degrees Celsius, before plateauing within the desired temperature range. Due to the overshooting, some of the plant material may become pyrolyzed.

In accordance with some applications of the present invention, a two-stage heating process is applied to plant material within a vaporizer, e.g., as indicated by the solid curve shown in FIG. 8. Typically, in response to receiving a first input at the vaporizer (e.g., in response to the user pressing an ON switch on the vaporizer), the control circuitry of the vaporizer initiates a first heating step. Typically, the first heating step is a rapid heating step (e.g., a heating step in which the capsule that contains the plant material is heated at a rate of more than 50 degrees Celsius per second, or more than 100 degrees Celsius per second). Further typically, the control circuitry of the vaporizer is configured to terminate the first heating step, by withholding causing further temperature increase of the capsule, in response to detecting that the temperature of the capsule (which is indicative of the temperature of the plant material) has reached a first temperature. Typically, the first temperature is less than 95 percent, e.g., less than 90 percent, or less than 80 percent, of the vaporization temperature of the plant material. For example, when the vaporizer is used to vaporize cannabis, the control circuitry of the vaporizer may be configured to withhold causing further temperature increase of the capsule, in response to detecting that the temperature of the capsule has reached a first temperature that is less than 170 degrees Celsius (e.g., less than 160 degrees Celsius), e.g., a temperature that is between 140 and 170 degrees Celsius, or between 150 and 160 degrees Celsius.

By configuring the control circuitry to terminate the first, rapid heating stage as described above, even if there is overshoot, and the temperature of the capsule rises above the temperature at which the first heating stage was programmed to be terminated, the temperature of the capsule will typically still not rise above the pyrolysis temperature of the plant material. For example, as shown in FIG. 8, the control circuitry has been configured to withhold causing further temperature increase of the capsule in response to detecting that the temperature of the capsule has reached approximately 160 degrees Celsius. Initially (at approximately 1 second), there is an overshoot, and the temperature of the capsule reaches approximately 180 degrees Celsius. However, the temperature of the capsule then reaches a plateau of approximately 160 degrees Celsius, at about 2 seconds. For some applications, the control circuitry of the vaporizer generates an output to the user to indicate that the first stage of the heating has terminated. For example, the control circuitry may illuminate an indicator light, may cause the vaporizer to vibrate, and/or may emit an audio signal (e.g., a beep).

Subsequently, in response to a second input to the vaporizer, the control circuitry of the vaporizer initiates a second heating step (shown, on the solid curve in FIG. 8, to begin at approximately 4 seconds). Typically, between the end of the first stage of the heating process, and the initiation of the second stage of the heating process, the control circuitry maintains the temperature of the capsule at the first temperature. For some applications, the second stage of the heating is initiated automatically in response to inhalation of air from the vaporizer by a user. Alternatively, the second stage of the heating process may be initiated in response to a different input by the user (e.g., the user pressing the ON button a second time).

During the second heating step, the control circuitry typically heats the capsule at a slower rate than during the first stage of the heating process. For example, during the second stage of the heating process, the meshes of the capsules of the vaporizer may be heated at a rate of less than 50 degrees Celsius per second, e.g., less than 40 degrees Celsius per second. As shown in FIG. 8, during the second stage of the heating process (from 4 seconds to 6 seconds) the capsule is heated from approximately 160 degrees Celsius to 200 degrees Celsius.

In the second stage of the heating process, the control circuitry is configured to withhold causing further temperature increase of the capsule in response to detecting that the temperature of the capsule is between the vaporization temperature of the plant material and the pyrolysis temperature of the plant material. For example, when the vaporizer is used to vaporize cannabis, the control circuitry of the vaporizer is configured to withhold causing further temperature increase of the capsule, in response to detecting that the temperature of the capsule has reached a second temperature that is more than 180 degrees Celsius (e.g., more than 190 degrees Celsius), and/or less than 220 degrees Celsius (e.g., less than 210 degrees Celsius), e.g., a temperature that is between 180 and 220 degrees Celsius, or between 190 and 210 degrees Celsius.

For some applications, by performing the heating in the two-stage process described hereinabove, one or more of the following results are achieved:

1) By terminating the first (rapid) stage of the heating in response to the temperature of the capsule reaching less than 95 percent of the vaporization temperature, even if the heating overshoots, the plant material is not pyrolyzed, since the plant material is not heated to a temperature that is greater than the pyrolysis temperature.

2) Since the second stage of the heating is performed slowly, there is negligible overshooting in the second stage of the heating process, and therefore the plant material does not get pyrolyzed in the second stage of the heating process.

3) Since, during the first stage of the heating, the plant material has already been heated to a temperature that is relatively close the vaporization temperature, even though the second stage of the heating is slow, the time that is required to heat the plant material to the vaporization temperature, from the initiation of the second heating stage, is relatively short (e.g., less than two seconds).

4) Due to low heat conduction of the plant material, if the plant material is heated rapidly, this can give rise to non-uniform heating of the plant material. This can cause portions of the plant material that are near to the heating element(s) (e.g., the electrode(s)) to be pyrolyzed, and/or portions of the plant material that are further from the heating element(s) not to be vaporized. By withholding further heating of the plant material after the first temperature has been reached, and until the second input is received, heat is able to dissipate through the plant material (during the interim period between the first and second heating stages) before any portion of the plant material has been heated to the vaporization temperature. Furthermore, since the temperature increase during the second stage is relatively small, the temperature increase is able to dissipate through the plant material relatively quickly. Thus, relatively uniform heating of the plant material is achieved, such that most of the active ingredient within the plant material is vaporized, while there is substantially no pyrolysis of the plant material.

For some applications, inhalation from the vaporizer by the user is automatically detected by the control circuitry. After the first stage of the heating, there is typically a large difference between the ambient temperature and the temperature of the capsule that contains the plant material. As described hereinabove, between the end of the first stage of the heating process, and the initiation of the second stage of the heating process, the control circuitry maintains the temperature of the capsule at the first temperature. Since there is a large difference between the ambient temperature and the temperature of the capsule, the energy that is required to maintain the capsule (and the plant material therein) at a constant temperature is greater when the user is inhaling from the vaporizer than when the user is not inhaling. Therefore, for some applications, the control circuitry detects that the user is inhaling from the vaporizer by detecting an indication of an amount of energy that is required to maintain the temperature of the capsule (and the plant material therein) constant. For example, the control circuitry may detect variations in the duty cycle that is used to heat the capsule (and the plant material therein). Alternatively or additionally, the control circuitry may automatically detect that the user is inhaling from the vaporizer by directly detecting the temperature of the capsule. Since, after the first stage of the heating, there is a large difference between the ambient temperature and the temperature of the capsule, airflow through the capsule may cause a measurable change in the temperature of the capsule. As described hereinabove, for some applications, the second stage of the heating process is initiated automatically in response to detecting inhalation from the vaporizer by the user.

Using a generally similar technique to that described hereinabove, for some applications, the control circuitry detects a rate and/or volume of air flow through the vaporizer, by detecting an indication of an amount of energy that is required to maintain the temperature of the capsule (and the plant material therein) constant. For some applications, in response to the detected rate of air flow through the vaporizer, the control circuitry calculates that dosage of the active substance that has been administered to the subject. As described hereinabove, for some applications, a healthcare professional may input instructions into the control circuitry that control the amount of airflow through the vaporizer that is permitted during each use of the vaporizer, and/or the amount of airflow through the vaporizer that is permitted within a given time period (e.g., per hour, or per day). Alternatively or additionally, the control circuitry may control the heating rate per unit air flow, as described hereinabove.

For some applications, in response to detecting that no inhalation has occurred over a given time period (e.g., a time period of between 0.5 seconds and 3 seconds), the temperature of the capsule is reduced to below the vaporization temperature of the plant material. For example, during use of the vaporizer, the user may stop inhaling for a given time period, due to coughing, and/or due to irritation caused by the plant material. By reducing the temperature to below the vaporization temperature, wastage of the active ingredient during this period is reduced, such that the user is able to receive the prescribed dosage of the active ingredient.

As indicated by the solid curve in FIG. 8, between approximately 8 seconds and 10.5 seconds the control circuitry causes the temperature of the capsule to be lowered to below the vaporization temperature. This may be performed in response to detecting that no inhalation has occurred over a given time period (as described hereinabove), and/or in response to a user input (e.g., in response to the user pressing a button). From approximately 10.5 seconds to 13.5 seconds, the capsule is heated back to the vaporization temperature. This may be performed in response to detecting that inhalation has resumed and/or in response to a user input (e.g., in response to the user pressing a button). Between approximately 14.5 seconds and seconds the control circuitry again causes the temperature of the capsule to be lowered to below the vaporization temperature. This may be performed in response to detecting that no inhalation has occurred over a given time period, and/or in response to a user input (e.g., in response to the user pressing a button).

Although vaporizer 20 has been described as using resistive heating of electrode(s) 48 to heat capsule 42, for some applications, alternative or additional heating elements and heating techniques are used to heat the capsule. For example, a laser emitter may act as a heating element by directing a laser beam at the capsule, in order to heat the capsule. For some applications, a separate heating element that is housed inside the vaporizer is heated in proximity to the vaporization location, in order to provide conduction, convection, and/or radiation heating to the capsule.

For some applications, the vaporizer includes an indicator that indicates to the user how many unused capsules are housed within the vaporizer. Typically, the vaporizer is configured such that it can only be opened and/or refilled by a healthcare professional (e.g., a doctor, or a pharmacist). For some applications, rather than the vaporizer being configured to be refilled, some of the control components of the vaporizer are recyclable and are transferrable to an unused vaporizer, as described hereinabove. For some applications, the size of the capsules and/or the amount of plant material in each capsule that is to be provided to a given user may be determined by a healthcare professional. In addition, as described hereinabove, the vaporizer is typically programmable, such that only a certain dosage of the active ingredient may be released per use or within a given time period. In this manner, if the plant material that is used inside the vaporizer is a regulated substance (e.g., cannabis), control over the use of the substance may be maintained. For some applications, the vaporizer and/or the capsules include identifying marks or tags (e.g., an RFID or a barcode), such as to facilitate regulation and control of the use of the vaporizer and the capsule.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for heating a material to generate a vapor, comprising:
   a main body having a first end, an opposing second end, and a central longitudinal axis extending from the first end to the second end;
   a mouthpiece configured for placement at the first end of the main body, the mouthpiece defining an outlet for the vapor, the mouthpiece tapering in size with proximity to the outlet, the outlet being off-centered relative to the central longitudinal axis of the main body;
   a containment structure defining a cavity and holding the material within the cavity;
   a metallic mesh secured to the containment structure and extending across the cavity so as to contact the material;
   a first electrode and a second electrode within the main body and configured to establish an electrical connection with the metallic mesh;
   a power supply within the main body, the power supply configured to supply an electrical current to the metallic mesh via the first electrode and the second electrode to heat the material to generate the vapor; and
   a port at the second end of the main body and electrically connected to the power supply, the port configured to connect to an external power source to facilitate a charging of the power supply.

2. The apparatus of claim 1, wherein the main body has a sidewall defining a plurality of inlets for air.

3. The apparatus of claim 2, wherein the plurality of inlets are opposing apertures.

4. The apparatus of claim 1, wherein the main body defines a cylindrical chamber configured to receive the containment structure.

5. The apparatus of claim 1, wherein the mouthpiece has an elliptical cross-section.

6. The apparatus of claim 1, wherein the outlet of the mouthpiece is in a form of a single opening.

7. The apparatus of claim 1, wherein the outlet of the mouthpiece has a longitudinal axis that is parallel to the central longitudinal axis of the main body.

8. The apparatus of claim 1, wherein the outlet of the mouthpiece has a circular cross-section.

9. The apparatus of claim 1, wherein the cavity of the containment structure has a circular cross-section.

10. The apparatus of claim 1, wherein the material includes a fibrous medium.

11. The apparatus of claim 1, wherein the material includes nicotine.

12. The apparatus of claim 1, wherein each of the first electrode and second electrode includes two points configured to establish the electrical connection with the metallic mesh.

13. The apparatus of claim 1, wherein the power supply is a battery.

14. The apparatus of claim 1, further comprising:
   control circuitry within the main body,
   wherein the control circuitry is configured to receive data via the port.

15. The apparatus of claim 1, further comprising:
   a first spacing element and a second spacing element on the containment structure.

16. The apparatus of claim 15, wherein the first spacing element and the second spacing element are diametrically opposed on the containment structure.

17. The apparatus of claim 15, wherein the first spacing element and the second spacing element protrude toward the outlet of the mouthpiece.

18. The apparatus of claim 15, wherein an exposed portion of the metallic mesh is between the first spacing element and the second spacing element.

19. The apparatus of claim 15, wherein each of the first spacing element and the second spacing element includes a curved side that is aligned with an adjacent curved side of the containment structure.

20. The apparatus of claim 15, wherein the first spacing element includes a first linear edge, the second spacing element includes a second linear edge, and the first linear edge and the second linear edge are parallel.

* * * * *